United States Patent [19]

Lessner et al.

[11] 4,239,391
[45] Dec. 16, 1980

[54] MODULAR MOTORIZED POLARIZERS FOR A SPECTROFLUOROMETER

[75] Inventors: David L. Lessner, Baltimore; James H. Macemon, Severna Park; George M. Coker, Jr; Charles E. Hodgson, both of Silver Spring, all of Md.

[73] Assignee: Baxter Travenol Laboratories, Inc., Deerfield, Ill.

[21] Appl. No.: 29,317

[22] Filed: Apr. 12, 1979

[51] Int. Cl.³ ............................. G01J 3/30; G01J 4/00
[52] U.S. Cl. ..................... 356/318; 356/366
[58] Field of Search ............... 356/317, 318, 366, 367, 356/368; 350/159

[56] References Cited
U.S. PATENT DOCUMENTS

| | | |
|---|---|---|
| 3,177,761 | 4/1965 | Redner . |
| 4,076,420 | 2/1978 | De Maeyer et al. .................. 356/73 |
| 4,082,459 | 4/1978 | Wolfe ..................................... 356/317 |

*Primary Examiner*—Alfred E. Smith
*Assistant Examiner*—Janice A. Howell
*Attorney, Agent, or Firm*—Robert A. Benziger; Paul C. Flattery; George H. Gerstman

[57] ABSTRACT

The input polarizer and the output polarizer of a spectrofluorometer are each mechanically identical except for the optical elements, and are constructed as modules which plug into a spectrofluorometer base. Each of the polarizer modules includes a polarizing filter that is rotatable and a self-contained motor drive for rotating the polarizing filter. Each of the motor drives comprises an electric motor mounted on the respective module, a pulley mounted on the respective module and rotatable with actuation of the electric motor, a loop coupling the pulley to the polarizing filter for rotation of the filter with rotation of the pulley, and means for enabling the filter to rotate exactly 90° in opposite directions.

19 Claims, 9 Drawing Figures

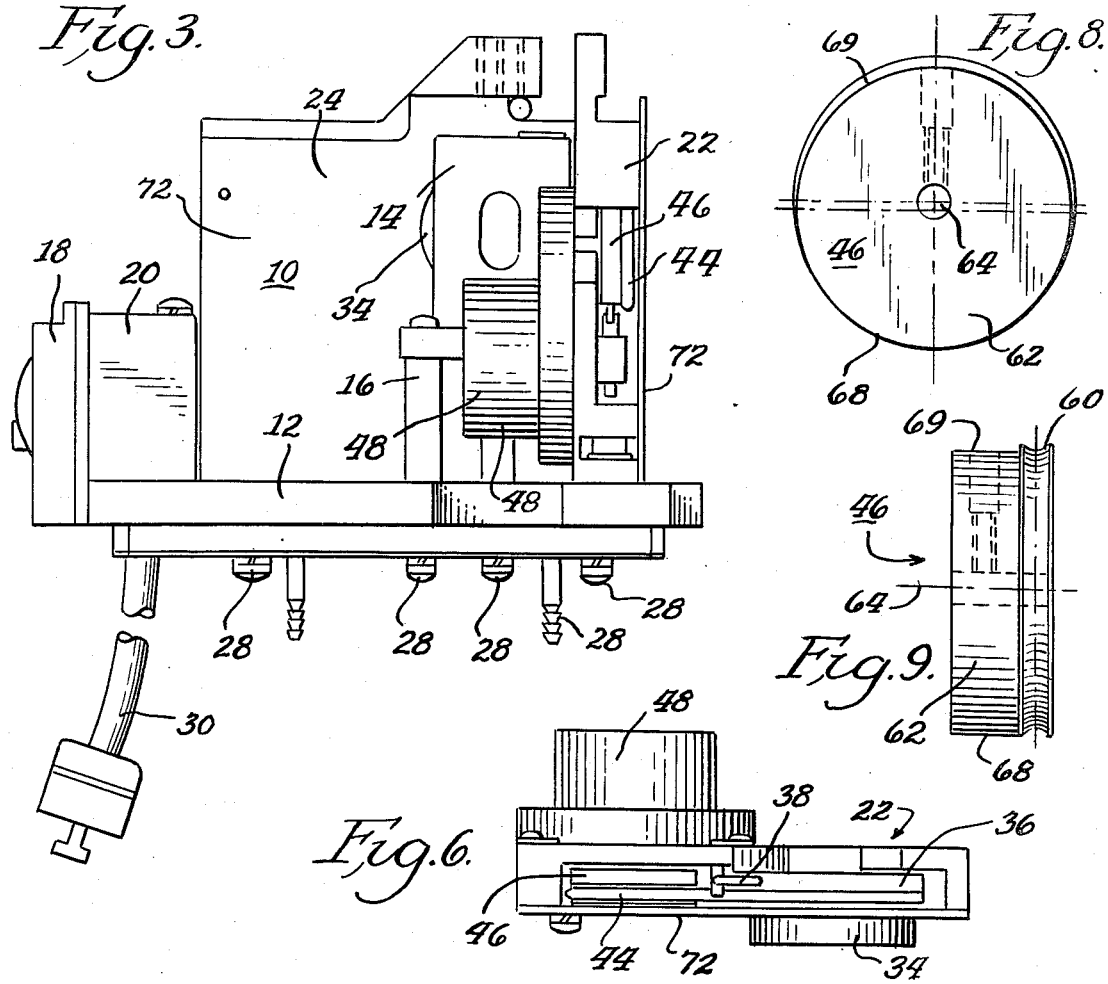

MODULAR MOTORIZED POLARIZERS FOR A SPECTROFLUOROMETER

BACKGROUND OF THE INVENTION

The present invention concerns an improved polarizer assembly for a spectrofluorometer and, more particularly, a novel polarizer assembly in which the input polarizer and the output polarizer are each modular and have self-contained motor drives.

Known in the art is a spectrofluorometer which includes an excitation monochromator which directs a light beam from a suitable light source through an excitation or input polarizer to a sample, from the sample through an emission or output polarizer and a depolarizer to an emission monochromator and to a detector. In polarization measurements, a fluorescent solution is excited by the beam of light whose electric vector is polarized vertically with the excitation polarizer. Since the electric and magnetic vector components of the light beam are always perpendicular to each other and have equivalent magnitudes, only the electric vector is specified. The vertically polarized light will excite only those sample molecules with vectors that are not perpendicular to the direction of polarization. The intensity of the two linearly polarized components of the fluorescent light emitted by the sample is measured by orienting the emission polarizer so as to transmit one component and then the other.

Thus in polarization measurements, the polarization of the generated light, which is emitted from the sample when polarized light is directed into the sample, may be indicative of the size of the particles in the sample. Prior art spectrofluorometers typically include an excitation (input) polarizer and an emission (output) polarizer with each of the polarizers comprising a polarizing filter that is rotatable between a vertical position and a horizontal position. In one application, a depolarizer is associated with the emission polarizer for depolarizing the emitted light from the sample which is then passed to a detector, such as a photomultiplier tube. In other applications, the depolarizer replaces either the emission or excitation polarizer.

Prior art polarizer assemblies were not constructed on a fully modular basis and did not include polarizer modules that were easily rearranged to perform alternate functions. Prior art motorized polarizers typically had the motor mounted to a base and a mechanical drive was coupled to each of the polarizers, thereby requiring that the drive be disconnected in order to remove the respective polarizer. Further, in prior art polarizer systems, in order to achieve 90° rotation in some instances the motor would be energized for a time duration sufficient to ensure that the travel had been completed. In other instances, a switch closure would be provided in order to deenergize the motor. Prior art polarizer assemblies which were not motorized would typically require the operator manually to move the polarizer 90° from a vertical position to a horizontal position.

It is an object of the present invention to provide a modular polarizer assembly in which the polarizers can be located in alternate positions on a mounting base for various functions.

Another object of the present invention is to provide modular polarizers which each have self-contained motor assemblies.

A further object of the present invention is to provide a system in which the polarizer filters of a polarizer assembly are motor driven with means for ensuring that the filters rotate exactly 90° as required.

Other objects and advantages of the present invention will become apparent as the description proceeds.

SUMMARY OF THE INVENTION

The present invention is particularly suited for use in a spectrofluorometer including an excitation monochromator, an emission monochromator and a base supporting a cell holder through which a light beam is transmitted. In accordance with the present invention, the improvement comprises a first polarizer module including a polarizing filter that is rotatable and including a motor drive for rotating the filter. The first polarizer module has plug-in means for rapid plug-in connection to the base.

A second polarizer module is provided including a polarizing filter that is rotatable and also including a motor drive for rotating the filter. The second polarizer module has plug-in means for rapid plug-in connection to the base.

One of the first and second polarizer modules is adapted for positioning between the excitation monochromator and the sample and the other of the first and second polarizer modules is adapted for positioning between the sample and the emission monochromator.

In the illustrative embodiment, the first and second polarizer modules are mechanically identical except for the optical elements. The motor drive for each of the first and second polarizer modules is self-contained by the respective polarizer module.

In the illustrative embodiment, each of the motor drives comprises an electric motor mounted on the respective module. A pulley is mounted on the respective module and is rotatable with actuation of the electric motor. A loop couples the pulley to the polarizing filter for rotation of the filter with rotation of the pulley. Means are provided for preventing the filter from rotating past a first predetermined point in a first direction and for preventing the filter from rotating past a second predetermined point in the opposite direction. In the illustrative embodiment, the first and second predetermined points are located so as to permit only 90° rotation of the filter.

In the illustrative embodiment, the preventing means comprises a pair of spaced pins carried by the polarizing filter for engagement with abutment means mounted on the module. A plurality of switches are mounted on the module and are operative in response to rotation of the filter for controlling energization of the electric motor. The motor is operative to continue rotating notwithstanding engagement of the respective pin carried by the filter with the abutment means mounted on the module, whereby the pin will be forced into full engagement with the abutment means. The pulley includes a cam positioned to operate a motor control switch after the respective pin has engaged the abutment means.

A more detailed explanation of the invention is provided in the following description and claims, and is illustrated in the accompanying drawings.

BRIEF DESCRIPTION OF THE DRAWINGS

FIG. 3 is a side elevational view thereof, taken from the right side of FIG. 1;

FIG. 4 is a rear elevational view of a polarizer module constructed in accordance with the principles of the present invention;

FIG. 5 is a side elevational view thereof;

FIG. 6 is a top plan view thereof;

FIG. 7 is a bottom plan view thereof;

FIG. 8 is a front elevational view of the cam pulley used with the polarizer module of FIGS. 4-7; and FIG. 9 is a side elevational view thereof, taken from the right side of FIG. 8.

DETAILED DESCRIPTION OF THE ILLUSTRATIVE EMBODIMENT

Figure 2:
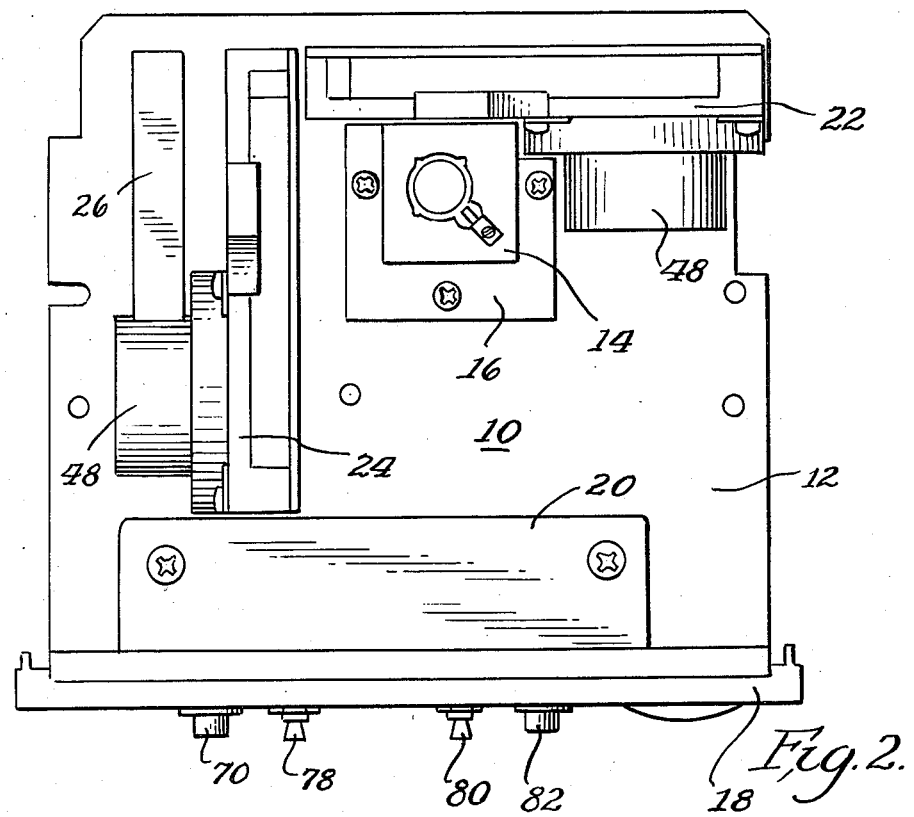
FIG. 2 is a top plan view thereof.
Figure 1:
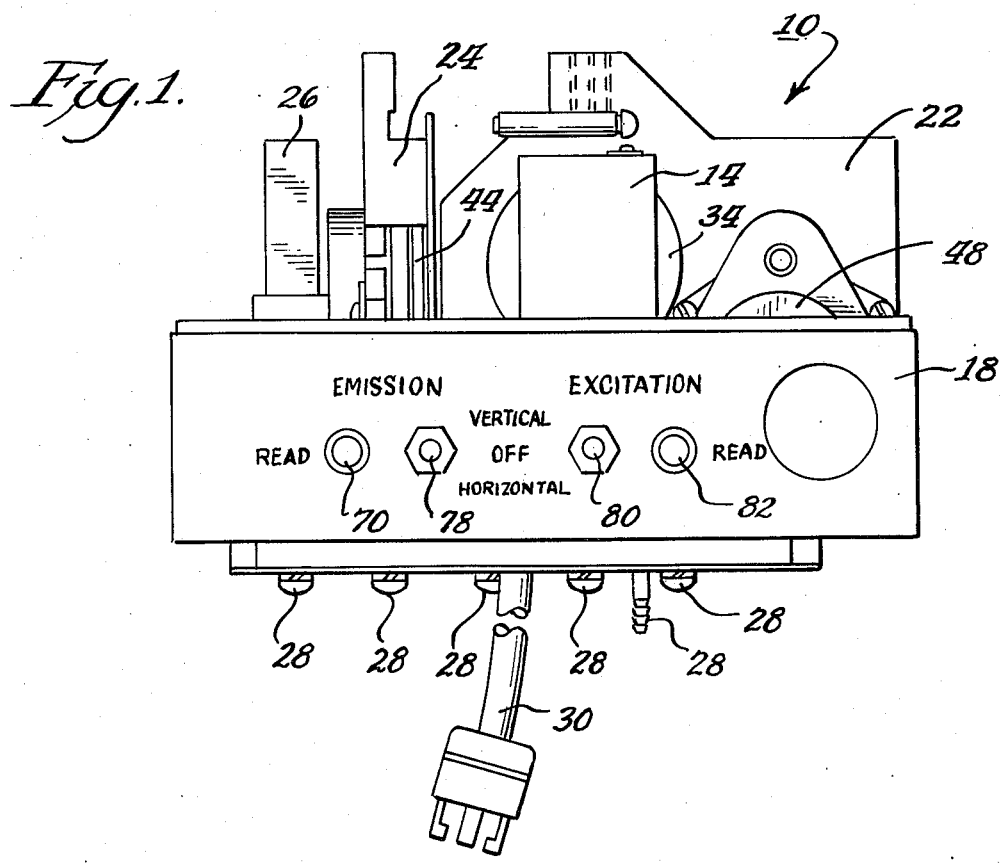
FIG. 1 is a front elevational view of a sample compartment for a spectrofluorometer, with the sample compartment including a cell holder and a pair of modular motorized polarizers constructed in accordance with the principles of the present invention.

Referring to the drawings, the sample compartment 10 illustrated in FIGS. 1-3 includes a base 12 upon which a cell holder 14 is supported by means of suitable supporting structure 16, a front plate 18 connected to base 12, a housing 20 for enclosing portions of the switches, lamps and wiring for the front panel controls, an excitation (or input) polarizer module 22, an emission (or output) polarizer module 24 and a depolarizer module 26. Sample compartment 10 is electrically and mechanically coupled to the spectrofluorometer by means of suitable connectors 28 and an electrical line 30.

Polarizer modules 22 and 24 and depolarizer module 26 are each of the plug-in type, having male pins which plug into female sockets defined by base 12. Polarizer modules 22 and 24 are mechanically identical with each other except for the optical elements. For purposes of simplicity, only polarizer module 22 will be described, it being understood that polarizer module 24 is mechanically identical thereto as stated above.

Referring now to FIGS. 4-7 in particular, polarizer module 22 includes a rotatable polarizer filter 32 contained within a filter retainer 34. Filter retainer 34 forms part of a surrounding filter holder 36 which carries radially extending pins 38, 40 and 42. The circumference of the filter holder assembly is slotted to receive a loop 44 in the form of an O-ring which is also coupled to cam pulley 46. Cam pulley 46 is driven by a reversible electric motor 48.

Three microswitches 50, 52 and 54 are mounted on the polarizer assembly for cooperation with the moving parts for energizing and deenergizing the electric motor 48 as required. Thus microswitch 50 is positioned for engagement with the cam surface of cam pulley 46, microswitch 52 is positioned for engagement with pin 42 and microswitch 54 is positioned for engagement with pin 40. As best seen in FIG. 4, pin 38 is operable between a position in which it engages stop pin 56 and a position in which it engages a set screw 58. Rotation of pin 38 from stop pin 56 to set screw 58 will provide a 90° rotation.

Cam pulley 46 is illustrated in detail in FIGS. 8 and 9. It is seen that the cam pulley includes a pulley slot 60 for receiving O-ring 44 and a cam portion 62 which is offset with respect to the central axis 64 for engaging arm 66 of microswitch 50 when the major portion 68 of cam portion 62 faces arm 66 and for missing arm 66 when the other portion 69 of cam portion 62 faces arm 66.

When the filter assembly is rotated counterclockwise to rotate pin 38 from set screw 58 to stop pin 56, the arm 66 of microswitch 50 will go upward into the recessed area 69 of the cam 46. Continued rotation will bring pin 42 into engagement with the arm of microswitch 52 prior to the arm 66 of microswitch 50 being allowed to move upwardly as it is engaged by minor surface 69 of cam 46. Actuation of both microswitches 50 and 52 will be indicated by "read" lamp 70 (FIG. 1) which will indicate to the operator that pin 38 has indeed contacted stop pin 56.

Thus the electric motor is energized so long as arm 66 is in its downward position. Since arm 66 is not allowed to move upward by cam surface 68, until subsequent to engagement of pin 38 with pin stop 56, the motor will continue to rotate (i.e., be overdriven) causing O-ring 44 to slip until cam surface 69 allows arm 66 to move up. This will ensure that pin 38 is in tight engagement with stop pin 56.

Likewise, when the filter assembly is rotated clockwise to move the pin 38 from stop pin 56 to set screw 58, pin 40 will engage the arm of microswitch 54. During the clockwise rotation of the filter, arm 66 is in its downward position and cam surface 68 does not allow arm 66 to move upward until subsequent to engagement of pin 40 with the arm of microswitch 54. Thus the motor will continue rotating after pin 38 has engaged set screw 58 causing belt 44 to slip and providing tight engagement of pin 38 with set screw 58. The overdriving of the motor ensures that the filter has been rotated exactly 90°.

Each of the polarizer modules is covered by means of a rear plate 72 which has been removed from the FIG. 4 illustration for clarity. Polarizer modules 22 and 24 each include an electrical connector 74 and male pins 76 which plug into suitable receptacles of base 12.

It can be seen that modular polarizers 22 and 24 can merely be plugged into base 12 and in order to rotate the polarizer lenses, the operator merely actuates switch 78 or switch 80 (FIGS. 1 and 2) located on the front panel 18. When switch 78 is actuated, after the filter has rotated and is in its proper position the "read" lamp 70 will be energized. Likewise, when switch 80 is actuated and the filter has rotated to its 90° position, "read" lamp 82 will be energized. Secure 90° rotation is provided due to the overdriving of motor 48 causing the respective pin to snugly engage its respective stop member after rotation.

Although an illustrative embodiment of the invention has been shown and described, it is to be understood that various modifications and substitutions may be made by those skilled in the art without departing from the novel spirit and scope of the present invention.

What is claimed is:

1. In a spectrofluorometer including an excitation monochromator, an emission monochromator and a base supporting a cell holder through which a light beam is transmitted, the improvement comprising, in combination:

a first polarizer module including a polarizing filter that is rotatable and including a motor drive for rotating the filter, said first polarizer module having plug-in means for rapid plug-in connection to said base;

a second polarizer module including a polarizing filter that is rotatable and including a motor drive for rotating the filter, said second polarizer module having plug-in means for rapid plug-in connection to said base; and one of said first and second polarizer modules being adapted for positioning between the excitation monochromator and the cell holder and the other of said first and second polarizer modules being adapted for positioning between the cell holder and the emission monochromator.

2. The device as described in claim 1, said first and second polarizer modules being mechanically identical except for the polarizing filter.

3. The device as described in claim 1, wherein the motor drive for each said first and second polarizer module is self-contained by the respective polarizer module.

4. The device as described in claim 1, wherein said plug-in means comprises outwardly extending plugs carried by each module for engagement with sockets defined by the base for completing electrical connections between the module and the base.

5. The device as described in claim 1, each of said motor drives comprising an electric motor mounted on the respective module, a pulley mounted on the respective module and rotatable with actuation of the electric motor, a loop coupling said pulley to said filter for rotation of said filter with rotation of said pulley, means for preventing said filter from rotating past a first predetermined point in a first direction and for preventing said filter from rotating past a second predetermined point in the opposite direction.

6. The device as described in claim 5, said first and second predetermined points being located so as to permit only 90° rotation of said filter.

7. The device as described in claim 5, said loop comprising an O-ring providing a belt-type drive.

8. The device as described in claim 5, said preventing means comprising a pair of spaced pins carried by said lens for engagement with abutment means mounted on the module.

9. The device as described in claim 5, including a plurality of switches mounted on the module and operative in response to rotation of the filter for controlling energization of the electric motor.

10. The device as described in claim 8, said motor being operative to continue rotating notwithstanding engagement of the respective pin carried by the filter with the abutment means mounted on the module, whereby the pin will be forced into full engagement with the abutment means.

11. The device as described in claim 10, said pulley including a cam positioned to operate a motor control switch after the respective pin has engaged said abutment means.

12. In a spectrofluorometer including an excitation monochromator, an emission monochromator and a base supporting a cell holder through which a light beam is transmitted, the improvement comprising, in combination:
a first polarizer module including a polarizing filter that is rotatable and including a motor drive for rotating the filter, said first polarizer module having plug-in means for rapid plug-in connection to said base;
a second polarizer module including a filter that is rotatable and including a motor drive for rotating the filter, said second polarizer module having plug-in means for rapid plug-in connection to said base;
said first and second polarizer modules being substantially mechanically identical;
the motor drive for each said first and second polarizer module being self-contained by the respective polarizer module;
each of said motor drives comprising an electric motor mounted on the respective module, a pulley mounted on the respective module and rotatable with actuation of the electric motor, a loop coupling said pulley to said filter for rotation of said filter with rotation of said pulley, means for preventing said filter from rotating past a first predetermined point in a first direction and for preventing said filter from rotating past a second predetermined point in the opposite direction, said first and second predetermined points being located so as to permit only 90° rotation of said filter;
said preventing means comprising a pair of spaced pins carried by said filter for engagement with abutment means mounted on the module;
a plurality of switches mounted on the module and operative in response to rotation of the filter for controlling energization of the electric motor, said motor being operative to continue rotating notwithstanding engagement of the respective pin carried by the filter with the abutment means mounted on the module, whereby the pin will be forced into full engagement with the abutment means; and
one of said first and second polarizer modules being adapted for positioning between the excitation monochromator and the cell holder and the other of said first and second polarizer modules being adapted for positioning between the cell holder and the emission monochromator.

13. In a spectrofluorometer including an excitation monochromator, an emission monochromator and a base supporting a cell holder through which a light beam is transmitted, the improvement comprising, in combination:
a polarizer assembly including a polarizing filter that is rotatable;
a reversible electric motor;
drive means coupled to said electric motor and to said filter for rotating said filter in response to rotation of said electric motor;
projecting means carried by said filter and abutment means mounted on said polarizer assembly, said projecting means being cooperatively engageable with said abutment means for limiting rotational movement of said filter in opposite directions;
switch means responsive to rotation of said filter for controlling energization of the electric motor; and
said drive means being cooperative with said switch means for overdriving the electric motor whereby said projecting means will be forced to engage said abutment means fully.

14. The device as described in claim 13, said drive means comprising a pulley that is rotatable with said electric motor and a belt-type loop coupling said pulley to said filter.

15. The device as described in claim 14, said projecting means comprising a plurality of spaced pins fixed to said filter.

16. The device as described in claim 15, said pulley including a cam positioned to operate said switch means to overdrive the electric motor.

17. The device as described in claim 16, said switch means including a first switch engagable by said cam and a pair of spaced switches engageable by said filter during rotation thereof, one of said switches of said pair being engaged when the filter rotates in a first direction and the other switch of said pair being engaged when the filter rotates in the opposite direction.

18. The device as described in claim 17, said first switch being engaged by said cam to stop the electric motor only after the filter has rotated to a predetermined position.

19. The device as described in claim 13, including a second polarizer assembly substantially mechanically identical to said aforementioned polarizer assembly, both of said polarizer assemblies being self-contained and having means for enabling plug-in connection with said base.

* * * * *